United States Patent
Panicheva et al.

(10) Patent No.: US 9,451,762 B2
(45) Date of Patent: Sep. 27, 2016

(54) FLORAL PRESERVATIVE

(71) Applicant: PuriCore, Inc., Malvern, PA (US)

(72) Inventors: Svetlana Panicheva, Downingtown, PA (US); Mark N. Sampson, Doylestown, PA (US); Ethan Solomon, Wilmington, DE (US); Ryan Gutzler, Drexel Hill, PA (US)

(73) Assignee: Puricore, Inc., Malvern, PA (US)

( * ) Notice: Subject to any disclaimer, the term of this patent is extended or adjusted under 35 U.S.C. 154(b) by 0 days.

(21) Appl. No.: 14/292,102

(22) Filed: May 30, 2014

(65) Prior Publication Data

US 2014/0274705 A1  Sep. 18, 2014

Related U.S. Application Data

(63) Continuation-in-part of application No. 12/845,046, filed on Jul. 28, 2010, now Pat. No. 9,006,140.

(60) Provisional application No. 61/229,163, filed on Jul. 28, 2009.

(51) Int. Cl.
*A01N 3/02* (2006.01)
*A01N 59/00* (2006.01)
*C02F 1/467* (2006.01)
*C02F 1/68* (2006.01)

(52) U.S. Cl.
CPC .............. *A01N 3/02* (2013.01); *A01N 59/00* (2013.01); *C02F 1/4674* (2013.01); *C02F 1/68* (2013.01); *C02F 2201/46115* (2013.01); *C02F 2209/05* (2013.01); *C02F 2209/06* (2013.01); *C02F 2305/04* (2013.01)

(58) Field of Classification Search
None
See application file for complete search history.

(56) References Cited

U.S. PATENT DOCUMENTS

| | | |
|---|---|---|
| 3,287,104 A | 11/1966 | Biggs |
| 4,278,715 A | 7/1981 | Romero-Sierra et al. |
| 5,080,707 A | 1/1992 | Ide et al. |
| 5,171,351 A | 12/1992 | Yamamoto et al. |
| 5,213,604 A | 5/1993 | Saito et al. |
| 5,284,818 A | 2/1994 | Shafer et al. |
| 5,366,954 A | 11/1994 | Bestwick et al. |
| 5,421,121 A | 6/1995 | Bestwick et al. |
| 5,500,403 A | 3/1996 | Shafer et al. |
| 5,536,155 A | 7/1996 | Futaki et al. |
| 5,580,840 A | 12/1996 | Harms et al. |
| 5,599,571 A | 2/1997 | Estrada |
| 5,635,443 A | 6/1997 | Lesenko |
| 5,679,617 A | 10/1997 | Hanafusa et al. |
| 5,723,406 A | 3/1998 | Larose et al. |
| 5,817,600 A | 10/1998 | Carstairs et al. |
| 5,961,886 A | 10/1999 | Hashimoto et al. |
| 6,440,900 B1 | 8/2002 | Koermer et al. |
| 7,144,841 B2 | 12/2006 | Pius |
| 7,199,082 B1 | 4/2007 | Chapman et al. |
| 7,273,831 B1 | 9/2007 | Fleskes et al. |
| 7,345,008 B1 | 3/2008 | Suzuki et al. |
| 2006/0140998 A1 | 6/2006 | Nakanishi et al. |
| 2007/0203050 A1* | 8/2007 | Oetter et al. ................. 510/424 |
| 2007/0231247 A1 | 10/2007 | Bromberg et al. |
| 2009/0008268 A1 | 1/2009 | Salathe et al. |
| 2011/0028319 A1 | 2/2011 | Panicheva et al. |
| 2012/0237616 A1 | 9/2012 | Panicheva et al. |

FOREIGN PATENT DOCUMENTS

| | | |
|---|---|---|
| DE | 10 2006 043267 | 3/2008 |
| WO | 03/075638 | 9/2003 |
| WO | 2004/027116 | 4/2004 |

OTHER PUBLICATIONS

Hammer et al., "Postharvest Control of Botrytis cinerea Infections on Cut Roses Using Fungistatic Storage Atmospheres" J. Amer. Soc. Hort. Sci. 115 (1): 102-107 (1990).

Macnish et al., "Sodium hypochlorite: A promising agent for reducing Botrytis cinerea infection on rose flowers" Postharvest Biology and Technology 58: 262-267 (2010).

Mueller et al., "Evaluation of Electrolyzed Oxidizing Water for Management of Powdery Mildew on Gerbera Daisy" Plant Disease 87: 965-969 (Aug. 2003).

Myresiotis et al., "Resistance of Botrytis cinerea Isolates from Vegetable Crops to Anilinopyrimidine, Phenylpyrrole, Hydroxyanilide, Benzimidazole, and Dicarboximide Fungicides" Plant Disease 91: 407-413 (Apr. 2007).

Al-Haq et al, "Applications of Electrolyzed Water in Agriculture & Food Industries" Food Science Technologies Res. 11 (2) pp. 135-150 (2005).

Anwar-Ul-Haq et al, "Effect of Nitrogen, Phosphorus and Potassium on Vegetative and Reproductive Growth of Rose (*Rosa centifolia*)" International Journal of Agriculture & Biology, vol. 1, No. 1 / 2 (1999) 27-29.

Buck et al., "In Vitro Fungicidal Activity of Acidic Electrolyzed Oxidizing Water" Plant Disease vol. 86, No. 3, pp. 278-281 (Mar. 2002).

Clark et al, "Efficacy of super-oxidized water fogging in environmental decontamination" Journal of Hospital Infection 64 (2006) 386-390.

(Continued)

*Primary Examiner* — Abigail Fisher
*Assistant Examiner* — Frank Choi
(74) *Attorney, Agent, or Firm* — Stradley Ronon Stevens & Young, LLP

(57) ABSTRACT

An electrochemically treated solution and method for cut flower and plant preservation, the solution having potassium, hypochlorous acid, dissolved oxygen, and a surfactant.

9 Claims, No Drawings

(56) References Cited

OTHER PUBLICATIONS de la Riva et al., "Treatment with Peracetic Acid Extends the Vase Life of Lisianthus (*Eustoma grandiflorum*) Flowers" HortScience 44(2): 418-420 (2009).
Excerpt of Oxford Dictionary of Chemistry (2004), Potassium Chlorate, p. 457.
Gast, Karen L.B. "Postharvest Handling of Fresh Cut Flowers and Plant Material" http://www.ksre.ksu.edu/library/hort2/mf2261.pdf Kansas State University Agricultural Experiment Station and Cooperative Extension Service (May 1997) 1-12.
Harada, "Behavior of Hydrogen Peroxide in Electrolyzed Anode Water," Biosci., Biotechnol., Biochem. (2002), vol. 66, No. 9, pp. 1783-1791.
Hur et al., "Inhibitory Effects of Super Reductive Water on Plant Pathogenic Fungi" Plant Pathology Journal 18(5); pp. 284-287 (2002).
Iftikhar Ahmad, Postdoc Scholar (NCSU), "When Should I Harvest and How Do I Handle My Flowers" NC State Horticulture Innovative Education, Research & Extension (Mar. 2013) http://www.ascfg.org/images/stories/ahmad.pdf.
International Search Report and Written Opinion dated Dec. 22, 2011 for corresponding international application No. PCT/US2010/043495.
Jones et al., Pulsing with Triton X-100 Improves Hydration and Vase Life of Cut Sunflowers (*Helianthus annuus* L.) HortScience 28(12): 1178-1179, 1993.
Kates et al., "Indigenous multiresistant bacteria from flowers in hospital and nonhospital environments" American Journal of Infection Control, vol. 19, No. 3, Jun. 1991, 156-161.
Kemme, "Preserving Cut Flowers," University of Illinois Extension Master Gardener News Column (2007).
Larson, Roy A. (editor), Introduction to Floriculture Second Edition, Academic Press, Inc. San Diego, CA (1980, 1992) pp. 11, 13, 51, 79, 88 and 91.
Loshon et al., "Analysis of the killing of spores of Bacillus subtilis by a new disinfectant, Sterilox®" Journal of Applied Microbiology 91 (2001) 1051-1058.
Martin and Gallagher "An investigation of the efficacy of super-oxidised (Optident/Sterilox) water for the disinfection of dental unit water lines" British Dental Journal vol. 198, No. 6 (Mar. 26, 2005) 353-354.
Melly et al., "Analysis of the properties of spores of Bacillus subtilis prepared at different temperatures" Journal of Applied Microbiology 92 (2002) 1105-1115.
Middleton et al, "Comparison of a solution of super-oxidized water (Sterilox®) with glutaraldehyde for the disinfection of bronchoscopes, contaminated in vitro with *Mycobacterium tuberculosis* and *Mycobacterium avium*-intracellulare in sputum" Journal of Hospital Infection 45 (2000) 278-282.
Nakagawara S. et al., "Spectroscopic Characterization and the pH Dependence of Bactericidal Activity of the Aqueous Chlorine Solution" Analytical Sciences, Aug. 1998, vol. 14, The Japan Society for Analytical Chemistry, Tokyo, JP pp. 691-698.
Park et al, "Evaluation of Liquid- and Fog-Based Application of Sterilox Hypochlorous Acid Solution for Surface Inactivation of Human Norovirus" Applied and Environmental Microbiology, vol. 73, No. 14 (May 2007) 4463-4468.

Pineau, Lionel "Etude 99-E-229 Sterilox/Lancer Preliminary Report" (1999) 1-6.
Reid, "Cut Flowers and Greens," Department of Environmental Horticulture, University of California, Davis, CA (2001).
Ruting, A. "Effects of Wetting Agents and Cut Flower Food on the Vase Life of Cut Roses" ISHS Acta Horticulturae 298: Hortifroid, V International Symposium on Postharvest Physiology of Ornamental Plants; Importance of Cold in Ornamental Horticulture (Dec. 1, 1991 ) (Abstract Only).
Selkon et al. "Evaluation of the antimicrobial activity of a new super-oxidized water, Sterilox®, for the disinfection of endoscopes" Journal of Hospital Infection 41 (1999) 59-70.
Selkon, J.B., "Development of a New Antiseptic for Treating Wound Infection" The Oxford European Wound Healing Course Handbook. Wound Healing Institute, Oxford, England (2002) 159-164.
Shetty et al. "Evaluation of microbicidal activity of a new disinfectant: Sterilox® 2500 against *Clostridium difficile* spores, *Helicobacter pylori*, vancomycin resistant *Enterococcus* species, *Candida albicans* and several *Mycobacterium* species" Journal of Hospital Infection 41 (1999) 101-105.
Silberbush and Lieth, "Nitrate and potassium uptake by greenhouse roses (*Rosa hybrida*) along successive flower-cut cycles: a model and its calibration" Scientia Horticulturae 101 (2004) 127-141.
Starck et al., "Effect of Fertiliser Nitrogen and Potassium Upon Yield and Quality of Carnations Grown in Peat and Sawdust" Abstract ISHS Acta Horticulturae 294: II Symposium on Horticultural Substrates and their Analysis, XXIII IHC http://www.actahort.org/members/showpdf?booknrarnr=294_31 as downloaded Jul. 23, 2009.
Tapper et al, "Atomic force microscopy study of the biocidal effect of super-oxidised water, Sterilox" Biofilm, vol. 3, Paper 4 (BF98004) (Jul. 10, 1998) Online Journal—URL: http://www.bdt.org.br/bioline/bf (printed from http://www.bioline.org.br/request?bf98004 Aug. 1, 2002) 16 pages (8 text, 8 photographs).
Tsegaw et al., "Influence of pulsing biocides and preservative solution treatment on the vase life of cut rose (*Rosa hybrida* L.) varieties" Ethiop. J. Appl. Sci. Technol. 2(2) 1-18 (2011).
van Doom "Vascular Occlusion in Stems of Cut Rose Flowers" Ph.D. Thesis, Agricultural University, Wageningen, The Netherlands 154 pages ISBN90-5485-139-2 (1993).
van Doom et al., "Alkylethoxylate surfactants for rehydration of roses and Bouvardia flowers" Postharvest Biology and Technology vol. 24, Issue 3, Apr. 2002, pp. 327-333 (Abstract Only).
van Doom et al., "Effect of antimicrobial compounds on the number of bacteria in stems of cut rose flowers" Journal of Applied Bacteriology 1990, 68, 117-122.
van Doom et al., "Effects of surfactants on the longevity of dry-stored cut flowering stems of rose, Bouvardia, and Astilbe" Postharvest Biology and Technology vol. 3, Issue 1, Jul. 1993, pp. 69-76 (Abstract Only).
Walker et al., "Microbiological Evaluation of a Range of Disinfectant Products to Control Mixed-Species Biofilm Contamination in a Laboratory Model of a Dental Unit Water System" Applied and Environmental Microbiology vol. 69, No. 6 (Jun. 2003) 3327-3332.
Zinkevich et al. "The effect of super-oxidised water on *Escherichia coli*" Journal of Hospital Infection 46 (2000) 153-156.

* cited by examiner

FLORAL PRESERVATIVE

CROSS REFERENCE TO RELATED APPLICATIONS

This application is a continuation-in-part of U.S. application Ser. No. 12/845,046, filed on Jul. 28, 2010, which claims the benefit of priority to U.S. Provisional Application No. 61/229,163, filed on Jul. 28, 2009, the contents of each of which are incorporated in this application by reference.

TECHNICAL FIELD

The invention relates to a preservative or watering solution for cut flowers and plants during their storage life. In particular, the invention relates to an electrochemically treated solution that extends the life of cut flowers and plants and prevents biofouling of the stems.

BACKGROUND OF THE INVENTION

Fresh cut flowers begin to loose their freshness as soon as they are cut. As such, there is a desire among floral retailers and consumers to lengthen the lifetime of cut flowers. Adding preservatives to water in which the fresh cut flowers are stored is a common practice in order to extend the life of the cut flowers. These preservatives range from powders to slurries to liquids of various ingredients.

The majority of current preservatives only provide for the vase-life extension of cut flowers. The preservatives are generally singular products or various combinations of sugars (or other nutrient sources for the cut plant), ethylene inhibitors, biocides, acids, and surfactants that are added to the water used to harvest, transport, and store cut flowers until retail or consumer handling. The purpose of adding these preservatives to plain water is to extend the time that flowers remain in a "sellable" condition after initial cutting from the plant in the field or greenhouse. Some of the preservatives are used before shipping, others are used to re-hydrate flowers, and yet other preservatives are used as transport solutions and for display at retail stores.

The most common preservative used for vase-life extension of flowers is the ubiquitous sachet that is provided to consumers as an add-on to most cut flower retail purchases. Despite the abundance of package shapes, sizes, and configurations, the sachet contains primarily sucrose and a granular acid, such as citric acid. The purpose of these two ingredients is to act as a source of nutrition for the plant (sucrose) and to reduce the pH of the water beneath the stems to inhibit the growth of microorganisms. The drawback to the use of this sachet is that many types of cut flowers do not require any nutritional source after harvest, and the addition of sugar to the water beneath the flower becomes a ready source of carbohydrate for bacterial and fungal growth. Many of the current preservatives do not provide biocide or odor control for flower and vase solutions and the addition of disinfectants is often needed. This can be seen by the increase in turbidity of the water over time.

To overcome the drawbacks of existing preservative solutions for cut flowers and plants, a new floral preservative is provided. An object of the present invention is to provide a preservative that improves the life of cut flowers and plants during storage, while transported, and when in vases or other containers. (As used in this document, and unless otherwise made clear, "vase life" means the life of the cut flowers and plants in any one or in any combination of these three phases: storage, transportation, and placement in vases or other containers.) Another object is to reduce the turbidity to the liquid into which the cut flowers and plants are placed. A related object is to combine the vase-life improvement and reduction in turbidity. Still another object is to improve water uptake. A further object is to improve the "cleanability" of vases and other containers in which cut flowers and plants are placed.

SUMMARY OF THE INVENTION

To achieve these and other objects, and in view of its purposes, the present invention provides, in one aspect, an electrochemically treated solution for cut flower and plant preservation comprising at least 99.5% by weight water, potassium chloride, hypochlorous acid, a surfactant, and dissolved oxygen. The solution has a pH of about 4.5 to 6.5.

Another aspect of the invention provides an electrochemically treated solution for cut flower and plant preservation comprising at least 99.5% by weight water, potassium chloride, hypochlorous acid, a surfactant having a concentration between 25 to 15,000 ppm, and dissolved oxygen. The solution has a pH of about 4.5 to 6.0.

Yet another aspect of the invention provides a method extending cut flower and plant life. The method provides an electrochemically treated aqueous solution comprising potassium chloride, hypochlorous acid, dissolved oxygen, and a surfactant. The solution has a pH of about 4.5 to 6.5. The method further includes the step of immersing a stem of the cut flowers or plants in the electrochemically treated aqueous solution.

It is to be understood that both the foregoing general description and the following detailed description are exemplary, but are not restrictive, of the invention.

DETAILED DESCRIPTION OF THE INVENTION

The invention provides an electrochemically treated solution used to treat cut flowers and plants, including non-flowering plants that are used in bouquets and other flower arrangements, and even cut trees and tree branches. Reference to cut flowers throughout the application also includes non-flowering plants. A fresh cut flower is still a living specimen even though it has been cut from the plant. As a living specimen, it conducts the regular reactions of photosynthesis and respiration, in significantly lower rates than compared to the living plant itself.

The solution provides an energy source for cut flowers and plants, for example, by supplying the plants with macro-nutrients, such as potassium. Furthermore, the solution is antimicrobial and controls both biofouling in floral storage solution and biofilm growth on the stems of flowers, retarding floral spoilage and protecting stems from rotting. The solution also prevents slime accumulation on the walls of storage containers and reduces the need for cleaning of those containers.

The solution is a preservative or watering solution for cut flowers that extends the storage life of the cut flowers. The storage life of the cut flowers is the time during which the cut flowers are kept in cold storage at a retailer or wholesaler. The vase life of the cut flowers is the time that a cut flower lasts in a customer's home, office, or other personal space. The result of using the electrochemically treated solution is the life of the cut flower is prolonged and the freshness of the cut flower is maintained over a longer period of time than if the flower were not in the solution or were in water alone.

The longevity of the vase life of cut flowers depends on the following factors: (1) inability of stems to absorb water due to xylem blockage, (2) excessive water loss from the cut flower, (3) short supply of carbohydrate to support respiration, (4) diseases, and (5) ethylene gas.

To prolong the vase life of fresh cut flowers, many preservatives have been used in the floral industry. In general, preservatives have three main functions: (1) provide carbohydrates to promote the respiration process, (2) supply bactericide to prevent microbial growth and blockage of the water-conducting cells in stems, and (3) acidify the storage solution for increasing the water flow through the stem. The result of using a floral preservative is that the vase life of cut flowers significantly increases.

The effectiveness of preservatives depends not only on the amount of light the flower receives and temperature at which the flower is stored, but also on other factors such as, for example, the amount and quality of water, the types of flowers, and the vase load, i.e., number of flowers per vase or number of bouquets per bucket. Respiration and photosynthesis of the flowers can be controlled by temperature and light. The electrochemical solution of this invention controls the respiration rate and photosynthesis rate of the cut flowers during the vase life of the flowers through the prevention of a potassium deficit.

Examples included in this application demonstrate the benefit of the electrochemical solution over commercial flower "food." Use of the electrochemical solution increases the vase life of select flowers. In addition, the turbidity of the water in which the flowers are stored is far lower with the use of hypochlorous acid compared to commercial flower food. A benefit of the decrease in turbidity is that it is easier to clean vases, buckets, and other containers (collectively, "vessels") in retail floral departments. The use of potassium chloride, as a solution for electrolytic production of hypochlorous acid, is beneficial because the potassium also acts as a macronutrient for the cut flower.

Potassium is a macro-element actively involved in the photosynthesis and respiration processes. Potassium regulates the rate of photosynthesis by its reaction with adenosine triphosphate (ATP). In addition, potassium plays a key role in transporting water and nutrients through cells. Plants depend upon potassium to regulate the opening and closing of stomates, the pores through which leaves exchange carbon dioxide ($CO_2$), water vapor, and oxygen ($O_2$) with the atmosphere. Proper functioning of stomates is essential for photosynthesis, water and nutrient transport, and plant cooling. When potassium moves into the cells around the stomates, the cells accumulate water and swell, causing the pores to open and allowing gases to move freely in and out. When water supply is short, potassium is pumped out of the cells. If the potassium supply is inadequate, plants are less able to absorb water.

Potassium's ability to stimulate the biochemical processes, including photosynthesis and respiration, may be used as a method of energy boost in cut flowers. Potassium injection activates sugar production by photosynthesis. Potassium may be added to the solution in the form of a potassium salt. Preferably, a potassium-based electrolyte is used to provide potassium ions as a nutrient source for cut flowers. More preferably, potassium chloride is used to provide potassium ions as a nutrient source for cut flowers.

Electrochemically processed potassium chloride solution has three main properties required for the preservation of fresh cut flowers: (1) it supplies biocide to prevent the microbial growth; (2) it provides optimal pH storage conditions; and (3) it boosts the energy in cut flowers, all of which result in better respiration and photosynthesis during vase life. Potassium chloride solution is processed through a diaphragm-based electrolytic cell, and enriched with hypochlorous acid and dissolved oxygen at a specific pH range, preferably, between 2.5 and 8 and, more preferably, between 3 and 6, and TDS (total dissolved solids) level, preferably, below 9 g/L and, more preferably, below 1.0 g/L. The electrochemically treated solution can be used as a universal preservative for cut flowers during the post harvesting, storage life, and vase life stages.

The energy boost provided to the cut flowers is often associated with the sugar component of floral preservatives. The reality is that not all cut flowers benefit from sugar. If the sugar concentration is too high, the flowers may be damaged. In order to overcome this issue, the electrochemical solution uses potassium to provide an energy boost and increase the vase life. In addition to using potassium in the solution, the combined effect of using hypochlorous acid and controlling the pH of the electrochemical treatment of the solution produces effective microbial control, i.e., prevents microbial growth. The hypochlorous acid is preferably supplied in a non-dissociated form. Another benefit of the electrochemically treated solution is that the use of an electrochemically treated potassium chloride solution, enriched with hypochlorous acid and dissolved oxygen, diminishes the negative effect of temperature fluctuations and water stress of cut flowers not only during storage life, but during vase life as well. The benefit is present if the flowers are stored in a commercial preservative or regular tap water. Yet another advantage of the electrochemically treated potassium chloride solution, enriched with hypochlorous acid and dissolved oxygen, is that not only does the solution provide a better quality of water but it also provides better quality stems and flowers. All types of flowers, including mixed bouquets, benefit from the solution.

The composition of the electrochemically treated solution comprises water, potassium chloride, hypochlorous acid, and dissolved oxygen. In one embodiment, the composition comprises at least 99.5% by weight water, 0.3% by weight or less potassium chloride, 0.01% by weight or less hypochlorous acid, and 0.001% by weight or less dissolved oxygen.

In another embodiment, the composition comprises at least 99.5% by weight water, 0.1% by weight or less potassium chloride, 0.3% by weight or less hypochlorous acid, and 0.002% by weight or less dissolved oxygen.

In one preferred embodiment, the solution also has a specific conductivity, or salinity, of about 0.2-18 mS/cm (milisiemens) and is produced at an optimized pH of about 2.5-10 and concentration of 5-600 ppm Available Free Chlorine (AFC) equivalent. In another preferred embodiment, the solution also has a specific conductivity of 0.2-18 mS/cm and is produced at an optimized pH of about 2.5-8 and concentration of 5-3,000 ppm AFC equivalent. AFC equivalent refers to a measure of all oxidants. In a more preferred embodiment, the solution has a specific conductivity of 0.2-2 mS/cm and is produced at an optimized pH of about 3-6 and concentration of 25-120 ppm AFC equivalent. In a most preferred embodiment, the solution has a specific conductivity of 1-2 mS/cm and is produced at an optimized pH of about 4-5 and concentration of 50 ppm AFC equivalent. In the solution, the pH is limited by potassium content in the low range and by ionization form in the high range. Salinity is limited by the flowers' sensitivity.

The components of the solution may be processed through an electrolytic cell to produce the electrochemically treated solution. Devices such as the Sterilox® 2200 may be used for the electrochemical treatment; however, any other device with an electrolytic cell may be used. The Sterilox® 2200 device is available from PuriCore, Inc. of Malvern, Pa.

The invention also provides a method of extending cut flower and plant life by providing an electrochemically treated aqueous solution having potassium, hypochlorous acid, and dissolved oxygen and immersing a flower stem in the electrochemically treated aqueous solution. No special handling or storage techniques are necessary. Storage of the flowers using this method may be done in any container, including vases and buckets at retailers, wholesalers, homes, offices, and other locations. The method may also include recutting of the cut flowers and replacing the solution or mixing the solution with water, the same solution, or other solutions. In addition, other parts of the flower, besides the stem, may be dipped or soaked in the solution.

The benefits of this method include reducing cloudiness and slime formation in the solution, controlling unpleasant odor formation in the stem and any flower attached to the stem, extending vase life of the stem and any flower attached to the stem, and limiting mold growth and slime formation on the stem. The vase life may be extended upwards of 15-20 days or 25 days or possibly more, depending upon the conditions where the stems and flowers are stored and how soon they are placed in the solution.

The following examples are presented to illustrate the invention. These examples are exemplary, not restrictive, of the invention. In the examples, the following terms have been used:

"(A) solution" means a solution generated using potassium chloride as the electrolyte having potassium chloride at 50 ppm of AFC, a pH range of 4-5, and a salinity range of 2-4 mS. The (A) solution has been commercialized under the trademark FloraFresh®.

"(B) comparative solution" means water with a solid granulated product used for floral preservation that was prepared following a manufacturer's instructions. "Unsellable" means that the flowers lost their leaves and/or were wilted.

"Storage life" means the time the cut flowers are kept in cold storage at a retailer or wholesaler.

"Home life" means the time that a cut flower lasts in a customer's home.

As stated above, otherwise made clear, "vase life" means the life of cut flowers and plants in any one or in any combination of these three phases: storage, transportation, and placement in vases or other containers.

Test Methods

AFC level in water and floral solutions was measured using a HACH® test kit (available from Hach Company of Loveland, Colo.).

Conductivity was measured with an Oakton® conductivity meter (available from Oakton Instruments of Vernon Hills, Ill.).

Dissolved oxygen was measured with a HACH® LDO meter (available from Hach Company of Loveland, Colo.) as an express method for evaluation of Biochemical Oxygen Demand in used solutions and dissolved oxygen in ready-to-use solutions.

pH was measured with an Oakton® pH meter (available from Oakton Instruments of Vernon Hills, Ill.).

Turbidity was measured using the HACH® DR4000/UV spectrophotometer and HACH® turbidity method 3750 (available from Hach Company of Loveland, Colo.

Water quality was evaluated based on two parameters: turbidity and level of dissolved oxygen.

EXAMPLES

Example 1

Effectiveness of Solution with Mixed Bouquets

Laboratory studies were performed to compare the effectiveness of an optimized electrochemically treated solution against the solid granulated product during storage and home life of mixed bouquets and maintaining the clarity of the bucket solution.

Run 1

Four vases were filled with 1.5 liters of either (A) solution generated using potassium chloride as the electrolyte or (B) comparative solution. Initially, mixed flower bouquets were trimmed by one inch from their stems, and two or three 15-stem bouquets were placed into the vases. A total number of stems were varied between 30 and 45 per each vase for each test solution type. One week later, the bouquets were arranged by placing into (A) solution, (B) comparative solution, and (C) tap water, one bouquet per vase.

Observations were documented on appearance and liveliness of flowers and their stems and clarity of solution. Individual flowers were removed from testing after being deemed "unsellable." Turbidity, conductivity, dissolved oxygen, and pH of solution, as well as total amount of intake water per vase, were also measured.

Flowers were topped every three days with either water, in the (B) comparative solution treated flowers, or with (A) solution in the (A) solution treated flowers during a first stage and with tap water in the (B) comparative solution treated flowers and (C) tap water treated flowers or with (A) solution in the (A) solution treated flowers during a second stage.

Run 2

Five vases were filled with 1.5 liters of either (A) solution or (B) comparative solution. Initially, mixed flower bouquets were trimmed by one inch from their stems, and one, two, or three 15-stem bouquets were placed into the vases. The total number of stems were varied between 15 and 45 per each vase for each test solution type. One week later, the bouquets were arranged by placing into tap water, one bouquet per vase.

Observations were documented on appearance and liveliness of flowers and their stems and clarity of solution. Individual flowers were removed from testing after being deemed "unsellable." Turbidity, conductivity, dissolved oxygen, and pH of solution, as well as total amount of intake water per vase, were also measured.

Flowers were topped every three days with either water, in the (B) comparative treated flowers, or with (A) solution in the (A) solution treated flowers during a first stage and with tap water during a second stage.

Results

The shelf life of flowers, contained at room temperature during storage life and home-life, was measured over 14 days. Most of the flowers treated with (B) comparative solution during storage life died within the 7 days of home life (over 14 days of trial). The quality of stems in control samples was observed for either (A) solution or (B) comparative solution treatment. Flowers treated with (A) solution showed no mold growth on their stems throughout the trial and the solutions demonstrated low turbidity.

In contrast, (B) comparative solution treated flowers showed cloudiness after 3 days of storage life. Visible mold was observed on the stems by the 5th day of vase life. Furthermore, significantly higher turbidity units were observed in the floral food solutions during storage life in both trials.

(A) solution demonstrated better performance under overstressed conditions by means of temperature (78° F. or 25° C.) and flowers load per vase. Flowers stored in (A) solutions during storage life showed better appearance during home life no matter how they were treated during that stage.

In contrast, (B) comparative solution treated flowers showed cloudiness after 3 days of storage in both high and low loaded vases. Furthermore, significantly higher turbidity units were observed in the floral food solutions at all stages. Stems of flowers demonstrated slime accumulation by the 5$^{th}$ day of both trials. Significant mold growth was observed by the end of the home life stage.

Overall, (A) solution provided better "home life" than (B) comparative solution, controlled cloudiness and slime formation of the solution and on the stems, protected stems from rotting and mold growth during home life, and controlled unpleasant odor formation in mixed bouquets during home life.

Example 2

Effectiveness of Solution with Cut Roses and Carnations

Laboratory studies were performed to compare the effectiveness of an optimized electrochemically treated solution against the solid granulated product in extending the shelf life of cut roses and carnations and maintaining the clarity of a bucket solution.

Example 2.1

Roses

Six vases were filled with 1.5 liters of either (A) solution generated using potassium chloride as the electrolyte or (B) comparative solution. Red roses were trimmed by one inch from their stems and 25 roses were placed into the vases. A total of 75 roses were used for each test solution type. Observations were documented on appearance and liveliness of roses and clarity of solution. Individual roses were removed from testing after being deemed "unsellable." Turbidity, conductivity, dissolved oxygen, and pH of solution were also measured. Flowers were topped every two days with either water in the (B) comparative solution treated flowers or with (A) solution in the (A) solution treated flowers.

Results

The shelf life of roses at room temperature was measured over 15 days. All control sample roses died within the 15 days. As shown in Table 1, equivalent shelf life of roses was observed for either (A) solution or (B) comparative solution treatment. Roses stored in (A) solutions showed no cloudiness throughout the trial and the solutions demonstrated low turbidity, as shown in Table 2.

In contrast, (B) comparative solution treated roses showed cloudiness after 2 days of storage, as shown in Table 2. Visible biofilm slime was observed on the sides of the vases by the 5th day and accumulated in the vases throughout the rest of the trial. Furthermore, Table 2 shows that significantly higher turbidity units were observed in the (B) comparative solutions.

TABLE 1

Shelf-life of Roses Treated with Either
(A) solution or (B) comparative solution

| | Number of Stems | |
|---|---|---|
| Days | (B) Comparative Solution | (A) Solution |
| 0 | 25 | 25 |
| 1 | 25 | 25 |
| 3 | 25 | 25 |
| 6 | 25 | 25 |
| 9 | 16 | 17 |
| 12 | 15 | 13 |
| 15 | 9 | 8 |

TABLE 2

Turbidity of Roses Treated with Either (A)
solution or (B) comparative solution

| | Average Turbidity (Units) | |
|---|---|---|
| Days | (B) Comparative Solution | (A) Solution |
| 0 | 0 | 0 |
| 1 | 10 | 0 |
| 3 | 16 | 0 |
| 6 | 16 | 0 |
| 9 | 23 | 3 |
| 12 | 23 | 3 |
| 15 | 32 | 3 |

Example 2.2

Carnations

Four Vases were filled with 1.5 liters of either (A) solution generated using potassium chloride as the electrolyte or (B) comparative solution. Carnations were trimmed by one inch from their stems and either 48 carnations (trial 1) or 34 carnations (trial 2) were placed into the vases. A total of 96 carnations (trial 1) or 68 carnations (trial 2) were used for each solution type. Observations were documented on appearance and liveliness of carnations and clarity of solution. Individual carnations were removed from testing after being deemed "unsellable." Turbidity, conductivity, dissolved oxygen, and pH of solution were also measured. Flowers were topped every two days with either water in the (B) comparative solution treated flowers or with (A) solution in the (A) solution treated flowers.

Results

The shelf life of carnations at room temperature was measured over either 14 or 17 days. As shown in Tables 3 and 5, equivalent shelf life of carnations was observed for either (A) solution or (B) comparative solution treatment in both trials. Carnations stored in (A) solution in both trials showed no cloudiness or slime accumulation, and low turbidity readings were measured for both trials, as shown in Tables 4 and 6.

In contrast, (B) comparative solution treated carnations showed cloudiness after 2 days of storage, and visible biofilm slime was observed on the sides of the vase after 5 days. Furthermore, significantly higher turbidity units were observed in both trials in the (B) comparative solutions, as shown in Tables 4 and 6. The stems of the carnations demonstrated slime accumulation by the 5$^{th}$ day of both trials.

TABLE 3

Shelf-life of Carnations Treated with Either (A) solution or (B) comparative solution in Trial 1

| | Number of Stems | |
|---|---|---|
| Days | (B) Comparative Solution | (A) Solution |
| 0 | 34 | 34 |
| 1 | 34 | 34 |
| 5 | 34 | 34 |
| 8 | 33 | 33 |
| 11 | 27 | 30 |
| 14 | 25 | 29 |

TABLE 4

Turbidity of Carnations Treated with Either (A) solution or (B) comparative solution in Trial 1

| | Average Turbidity (Units) | |
|---|---|---|
| Days | (B) Comparative Solution | (A) Solution |
| 0 | 0 | 0 |
| 1 | 0.5 | 0 |
| 5 | 5.5 | 0.5 |
| 8 | 3 | 1.5 |
| 11 | 11.5 | 0 |
| 14 | 44 | 6.5 |

TABLE 5

Shelf-life of Carnations Treated with Either (A) solution or (B) comparative solution in Trial 2

| | Number of Stems | |
|---|---|---|
| Days | (B) Comparative Solution | (A) Solution |
| 0 | 45 | 45 |
| 1 | 45 | 45 |
| 3 | 45 | 45 |
| 5 | 45 | 45 |
| 7 | 45 | 45 |
| 10 | 45 | 43 |
| 14 | 41 | 41 |
| 17 | 32 | 38 |

TABLE 6

Turbidity of Carnations Treated with Either (A) solution or (B) comparative solution in Trial 2

| | Average Turbidity (Units) | |
|---|---|---|
| Days | (B) Comparative Solution | (A) Solution |
| 0 | 0 | 0 |
| 1 | 8 | 1 |
| 3 | 8 | 2.5 |
| 5 | 12 | 1.5 |
| 7 | 9 | 3 |
| 10 | 95 | 6.5 |
| 14 | 190 | 5.5 |
| 17 | 213 | 13 |

Example 3

Effectiveness of the Solution with Surfactants

Surfactants aid in water uptake due to the reduction of surface tension. Water uptake improves the appearance of cut flowers by reducing wilting of flowers and leaves. In addition, many commonly used surfactants improve the potency of active antimicrobial ingredients. Surfactants may also aid in inhibiting the growth of fungi or bacteria in the vase and improving the "clean-ability" of vases following display of flowers.

The vase-life improvement and reduction in turbidity demonstrated with hypochlorous acid produced by electrolysis of potassium chloride has been described above. In another aspect of the invention, the hypochlorous acid produced by electrolysis of potassium chloride is combined with surfactants to improve water uptake and enhance vase-life extension. The use of the combination of ingredients in a formulation acts synergistically to provide an increase in vase-life and reduced turbidity of vase water. In addition, the invention results in improved "clean-ability" of vases, buckets, and containers greater than that of hypochlorous acid alone.

(D) solution, commercialized under the trademark FloraFresh®, consists of hypochlorous acid generated from a brine of potassium chloride at a concentration of approximately 6 grams KCl per liter of water. Additional items in (D) solution include potassium carbonate (for stabilization of hypochlorous acid) and a combination of dibasic and monobasic potassium phosphate as a buffer to maintain pH at approximately 5.0 when electrolytic production is complete. (D) solution is a concentrate intended for dilution at the customer site and is delivered as a solution of approximately 3,000 (specification 2,500-3,300) ppm AFC with a pH of about 5.0, but generally in the range of pH 4.5-6.5.

In this example, select surfactants are added to (D) solution at concentrations ranging from 25-15,000 parts per million (ppm) such that dilution at a rate of 1 part formulation to 50 parts water results in a surfactant concentration of 0.5-300 ppm in the finished product. In a preferred embodiment, the solution has a conductivity of 0.75 mS/cm. Surfactants can be selected from various classes including amphoteric (having both anionic and cationic portions on the same molecule), non-ionic (uncharged), and anionic surfactants (negative charge). Any type of surfactant may be useful, especially those that are known to be stable in an oxidative formulation (i.e., containing hypochlorous acid) over an extended period of time. In addition, surfactants that are known to promote stability in oxidative systems by minimizing loss of AFC are especially useful in this invention.

Amphoteric surfactants that are suitable for this application include, for example, amine oxides such as decylamine oxide, lauramine oxide, and myristamine oxide. Other amine oxides of various alkyl chain length (C8-C18) are also suitable in this application. These are available commercially from a number of vendors, for example the Ammonyx® line of surfactants (Ammonyx® DO, Ammonyx® LO, etc.) available from the Stepan Company of Northfield, Ill., or the Macat® line available from Mason Chemical Company of Arlington Heights, Ill. Other suitable surfactants in this class are tertiary amine oxides wherein the methyl groups have been replaced with longer chain saturated alkyl groups (C2-C12). Yet another group of amphoteric surfactants that are suitable for this application are the surfactant betaines consisting of alkyl betaines and alkyl amido betaines of various alkyl chain length. This class of surfactants are available commercially under the trade name Genagen® from Clariant International of Muttenz, Switzerland.

Non-ionic surfactants that are suitable for this application include, for example, ethoxylated octyl or nonylphenols such as the Triton® range of surfactants available from Dow Chemical of Midland, Mich. or ethoxylated linear alcohols such as the Bio-Soft® line available from Stepan of Northfield, Ill.). Additional non-ionic surfactants that are useful in this application are the block co-polymers of ethylene and propylene oxide available as Pluronic® surfactants from BASF of Florham Park, N.J.

Anionic surfactants that are suitable include, for example, alkyl or alkyl-phenyl sulfates, sulfonates, or phosphates. A preferred surfactant is linear alkyl benzene sulfonate, which is available under the Bio-Soft® trade name from Stepan of Northfield, Ill., or mono and di-alkyl diphenyl ether disulfonates such as those available as Dowfax® from Dow Chemical of Midland, Mich. Other linear, phenyl, or branched sodium or potassium sulfates or sulfonates are also suitable as surfactants for inclusion in the formulation.

In this Example, (D) solution is prepared, as described above, and one or more of the surfactants listed above are added at a concentration of between 25 and 15,000 parts per million. The product is then packaged as normal with instructions to dilute at the time of use by a factor of approximately 1:50 to give a final surfactant concentration of between 0.5 and 300 ppm.

Example 3.1

Effectiveness of Solution with Surfactant with Cut Roses

A vase-life study was conducted to determine the effect of adding surfactants to (D) solution. Red roses (variation Freedom) were purchased and transported to the laboratory with stems immersed in fresh water. Glass vases were filled with either 1 liter of water or (D) solution containing 10 parts per million (ppm) of select surfactants. (D) solution alone with no added surfactant was used as an additional control. One dozen roses were re-cut using a hand pruner (approximately 1-2 inches were removed from the bottom of the stem) and immediately placed into vases. Floral appearance was determined qualitatively on a daily basis. Microbial growth in the water beneath the roses was determined using an ATP luminometer (available from 3M of Maplewood, Minn.). Lower levels of ATP indicate reduced microbial growth. The table below indicates an assessment of roses following 7 days of display in the solutions indicated.

TABLE 7

Assessment of Roses Treated with Solutions As Indicated

| Treatment | Number of stems with bent necks (out of 12) | ATP - day 7 (RLU) | Flower Appearance |
| --- | --- | --- | --- |
| Tap Water | 3 | 195,295 | Dry |
| (D) solution alone | 1 | 51,033 | Dry |
| (D) solution + 10 ppm sodium alkane sulfonate | 0 | 8,734 | Good |
| (D) solution + 10 ppm sodium dodecyl benzene sulfonate | 1 | 213 | Good |
| (D) solution + 10 ppm potassium alkanoate | 0 | 15,886 | Slightly Dry |
| (D) solution + 10 ppm polyethoxy adduct | 1 | 4,958 | Dry |

As outlined in Table 7, above, roses in tap water alone appeared dry after 7 days. Three of the 12 roses in the tap water vase had bent necks, indicating poor water uptake. Roses held in (D) solution alone also had dry flowers, but only 1 in 12 had a bent neck. Two of the four surfactants added at 10 ppm resulted in flowers with good or only a slightly dry appearance and no incidence of bent necks after 7 days. The addition of 10 ppm sodium alkane sulfonate as well as 10 ppm of potassium alkanoate to (D) solution resulted in good flower appearance and no bent necks after 7 days of display.

The ATP data indicate a significant improvement in the ability of the formulation to inhibit microbial growth in the water beneath the rose stems. Tap water beneath the stems was visibly turbid after just a few days and at 7 days; ATP measurements indicated 195,295 Relative Light Units (RLU). (D) solution alone was slightly better at inhibiting microbial growth with a reading of 51,033 RLU. All of the formulations of (D) solution containing added surfactant had lower levels of ATP compared to the tap water and (D) solution controls.

Although the invention has been described in detail and with reference to specific embodiments and examples, it will be apparent to one skilled in the art that various changes and modifications can be made without departing from the spirit and scope of the invention. For example, the electrochemically treated solution may comprise additional components added before or after electrolysis to achieve certain properties. These additional components may include sugars, salts, surfactants, pH stabilizers, bactericides, fungicides, nutrients, and other preservatives. Thus, it is intended that the invention covers the modifications and variations of this invention provided they come within the scope of the appended claims and their equivalents. It is expressly intended, for example, that all ranges broadly recited in this document include within their scope all narrower ranges which fall within the broader ranges. It is also expressly intended that the steps of the methods of using the various solutions disclosed above are not restricted to any particular order.

The invention claimed is:

1. An electrochemically treated solution for cut flower and plant preservation consisting of:
   at least 99.5% by weight water;
   an effective amount of potassium chloride;
   an effective amount of but no more than 0.01% by weight hypochlorous acid, wherein the hypochlorous acid is supplied in an undissociated form;
   a surfactant, wherein the surfactant concentration is between 0.5 to 15,000 ppm; and
   an effective amount of dissolved oxygen, wherein the solution has a total dissolved solids level of no more than 9 g/L, has a conductivity of 0.2-18 mS, has 5-600 ppm of available free chlorine equivalent, and has a pH of about 4.5 to 6.0.

2. The solution of claim 1 wherein the surfactant is an amphoteric surfactant.

3. The solution of claim 1 wherein the surfactant is a non-ionic surfactant.

4. The solution of claim 1 wherein the surfactant is an anionic surfactant.

5. The solution of claim 1 wherein the surfactant concentration is between 0.5 to 300 ppm.

6. A method of extending cut flower and plant life comprising:
   providing an electrochemically treated aqueous solution that (a) consists of water, potassium chloride, hypochlorous acid, dissolved oxygen, and a surfactant, (b) has a total dissolved solids level of no more than 9 g/L, (c) has a conductivity of 0.2-18 mS, (d) has 5-600 ppm of available free chlorine equivalent, and (e) has a pH of 4.5 to 6.5; and
   immersing a stem of a cut flower or plant in the electrochemically treated aqueous solution.

7. The method of claim 6 wherein the step of immersing further comprises inhibiting microbial growth in a vessel containing a cut flower or a plant.

8. The method of claim 6 wherein the surfactant concentration is 25 to 15,000 ppm.

9. The method of claim 6 wherein the surfactant concentration is 0.5 to 300 ppm.

* * * * *